US00PP31018P2

(12) United States Plant Patent
Klemm et al.

(10) Patent No.: US PP31,018 P2
(45) Date of Patent: Nov. 5, 2019

(54) ***DIANTHUS* PLANT NAMED 'KLEDP17262'**

(50) Latin Name: *Dianthus caryophyllus*
Varietal Denomination: KLEDP17262

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,959

(22) Filed: May 30, 2018

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Barbara Campbell; CochranFreund & Young LLC

(57) ABSTRACT

A new *Dianthus* plant designated 'KLEDP17262' particularly distinguished by red-purple flowers with lighter red-purple borders and an upright habit, is disclosed.

1 Drawing Sheet

Genus and species: *Dianthus caryophyllus*.
Variety denomination: 'KLEDP17262'.

BACKGROUND OF THE NEW PLANT 'KLEDP17262'

The present invention comprises a new and distinct variety of *Dianthus*, botanically known as *Dianthus caryophyllus*, and hereinafter referred to by the variety name 'KLEDP17262'. 'KLEDP17262' originated from a whole plant mutation from the *Dianthus* parent 'KLEDP14206', also commercially known as OSCAR 'Purple Wings' (U.S. Plant Pat. No. 26,846) in June 2014 in The Netherlands.

In September 2014, 'KLEDP17262' was first vegetatively propagated by vegetative stem cuttings in Stuttgart, Germany and Latina, Italy. 'KLEDP17262' was found to reproduce true to type in successive generations of asexual propagation in Stuttgart, Germany via vegetative stem cuttings.

SUMMARY OF 'KLEDP17262'

The following are the most outstanding and distinguishing characteristics of 'KLEDP17262' when grown under normal horticultural practices in Stuttgart, Germany.

1. Red-purple flowers with lighter red-purple borders; and
2. An upright habit.

DESCRIPTION OF THE PHOTOGRAPH

This new *Dianthus* plant is illustrated by the accompanying photograph of a plant approximately 10-weeks-old and grown in a greenhouse in Stuttgart, Germany. The photograph shows the whole plant, including the flowers and foliage and buds of 'KLEDP17262' and was taken in March 2016 in Stuttgart, Germany. The colors shown are as true as can be reasonably obtained by conventional photographic procedures.

DESCRIPTION OF 'KLEDP17262'

The following detailed descriptions set forth the distinctive characteristics of 'KLEDP17262'. The data which define these characteristics were collected from asexual reproductions carried out in Stuttgart, Germany. Data was collected in April 2018 on 6-month-old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP17262'.

Parentage:
- *Mutation parent*.—'KLEDP14206', also commercially known as OSCAR 'Purple Wings' (U.S. Plant Pat. No. 26,846).

Plant:
- *Propagation type*.—Vegetative stem cuttings.
- *Time to produce a rooted young plant*.—10 to 14 days.
- *Rooting shape*.—Lanceolate.
- *Plant form*.—Upright.
- *Plant height*.—10.0 cm to 12.0 cm.
- *Plant diameter or spread*.—14.0 cm to 16.0 cm.

Lateral branches:
- *Length*.—7.0 cm to 9.0 cm.
- *Diameter*.—2.0 cm to 4.0 m.
- *Internode length*.—0.4 cm to 0.6 cm.
- *Number of internodes per branch/stem*.—4.
- *Node length*.—0.3 cm.
- *Node diameter*.—0.3 cm.
- *Texture*.—Smooth.
- *Color*.—RHS N137B (Green).
- *Branch/stem*.—Solid, circular.

Foliage:
- *Arrangement*.—Opposite.
- *Length*.—4.0 cm to 6.0 cm.
- *Width*.—0.6 cm to 0.8 cm.
- *Shape*.—Lanceolate.
- *Apex*.—Acute.
- *Base*.—Obtuse.

*Margin*.—Entire.
*Curvature of leaf*.—Weakly recurved.
*Texture* (*both upper and lower surfaces*).—Smooth.
*Immature leaf color*.—Upper surface: RHS 143A (Green). Lower surface: RHS 143B (Green).
*Mature leaf color*.—Upper surface: RHS 139A (Green). Lower surface: RHS N137B (Green).
*Venation pattern*.—Parallel.
*Venation color*.—Upper surface: RHS 139A (Green). Lower surface: RHS N137B (Green).
*Glaucosity of leaf*.—Medium.

Flowers:
*Flower type and habit*.—Double, round, small sprays.
*Fragrance*.—Present, sweet.
*Natural flowering season*.—Spring to fall.
*Position of flowers relative to the foliage*.—Slightly above.
*Number of flowers per spray*.—2 to 4.
*Flower longevity on the plant*.—10 to 12 days.
*Buds*.—Length: 1.8 cm to 2.0 cm. Diameter: 0.8 cm to 1.0 cm. Shape: Elliptic. Color: RHS 137A (Green) and RHS 143C (Green). Extrusion of the styles at the bud stage: Absent.
*Corolla*.—Quantity of petals and arrangement: 15 to 20 petals in several whorls. Corolla height: 1.5 cm to 2.0 cm. Diameter of flower: 3.0 cm. Petal length: 3.5 cm. Petal width: 1.4 cm to 1.6 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS 59B (Red-purple) with RHS 68B (lighter Red-purple) borders. Lower surface: RHS 68B (Red-purple) with RHS 62C (lighter Red-purple) borders. Mature: Upper surface: RHS 60A (Red-purple) with RHS 73B (lighter Red-purple) borders. Lower surface: RHS 73B (Red-purple) with RHS 69D (lighter Red-purple) borders.
*Calyx*.—Quantity of sepals and arrangement: Composed of 5 sepals, fused. Shape: Campanulate. Calyx height: 1.8 cm to 2.0 cm. Calyx diameter (at the apex): 0.8 cm to 1.0 cm. Calyx lobe length: 0.8 cm. Sepal texture (both upper and lower surfaces): Smooth. Sepal color: Upper surface: RHS 137A (Green). Lower surface: RHS 137D (Green).

Peduncles:
*Length*.—12.0 cm to 14.0 cm.
*Diameter*.—0.2 cm.
*Strength*.—Moderate.
*Texture*.—Smooth.
*Color*.—RHS N137A (Green).

Reproductive organs:
*Stamens*.—Quantity per flower: 3 to 5. Filament length: 0.5 cm to 0.7 cm. Filament color: RHS 2D (Yellow). Anther length: 0.1 cm. Anther diameter: 0.05 cm. Anther color: RHS 73C (Red-purple). Pollen amount: Sparse.
*Pistils*.—Quantity per flower: 1. Pistil length: 1.2 cm to 1.6 cm. Style length: 0.8 cm to 1.0 cm. Style color: RHS 69D (Red-purple). Quantity and shoulder of style: 3 styles without shoulder are present. Stigma shape: Filamentous. Stigma color: RHS 72C (Red-purple). Ovary size: 0.4 cm to 0.6 cm. Ovary shape: Oval. Ovary color: RHS 144C (Yellow-green). Ovary texture: Smooth.

Fruit and seed set: Seed is sometimes observed, but no information on the seed is available.

Disease and pest/insect resistance: No disease and pest/insect resistance observed.

COMPARISON OF 'KLEDP17262' WITH PARENTAL LINE AND KNOWN VARIETY

'KLEDP17262' is distinguished from the mutation parent as described in Table 1 and is distinguished from the commercial comparison 'KLEDP10111' (unpatented) in Table 2.

TABLE 1

Comparison with Parental Line

| Characteristic | 'KLEDP17262' | Mutation Parent 'KLEDP14206' |
|---|---|---|
| Petal color | Red-purple with lighter red-purple border | Purple with dark purple stripes and centers |

TABLE 2

Comparison with Similar Variety

| Trait | 'KLEDP17262' | 'KLEDP10111' |
|---|---|---|
| Flower color | Red-purple with lighter red-purple border | Pink with purple centers |

We claim:

1. A new and distinct variety of *Dianthus* plant designated 'KLEDP17262' as illustrated and described herein.

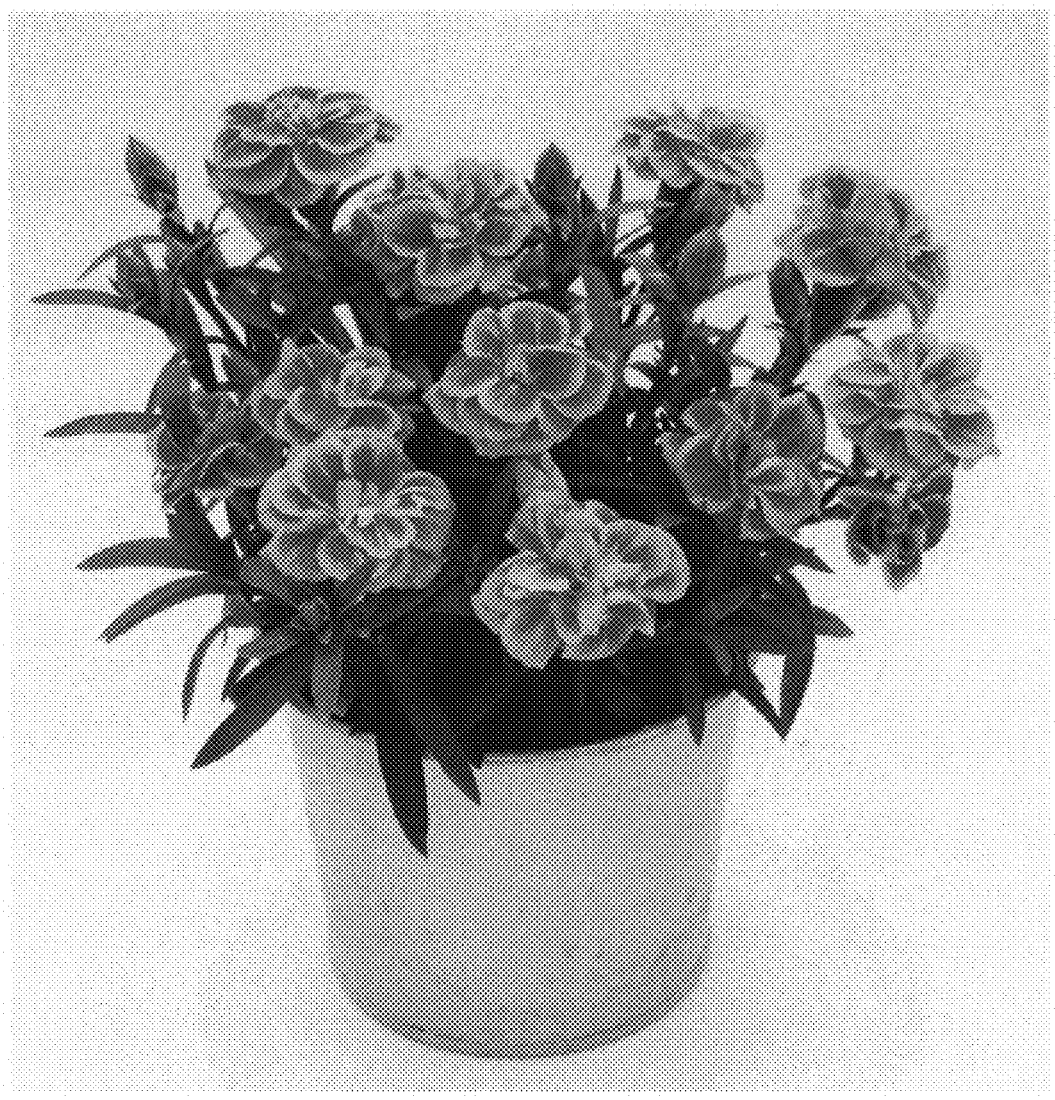

* * * * *